United States Patent [19]

Jegham et al.

[11] Patent Number: 5,589,476
[45] Date of Patent: Dec. 31, 1996

[54] IMIDAZOL-4-YLPIPERIDINE DERIVATIVES, THEIR PREPARATION AND THEIR APPLICATION IN THERAPEUTICS

[75] Inventors: Samir Jegham, Argenteuil; Gérard Defosse, Paris; Thomas A. Purcell, Montfort L'Amaury; Luc Even, Paris, all of France

[73] Assignee: Synthelabo, Le Plessis Robinson, France

[21] Appl. No.: 317,661

[22] Filed: Oct. 3, 1994

[30] Foreign Application Priority Data

Oct. 4, 1993 [FR] France .................. 93 11771

[51] Int. Cl.⁶ .................. C07D 498/12; C07D 498/16; A61K 31/535; A61K 31/435
[52] U.S. Cl. .................. 514/230.2; 544/101; 544/346; 540/556; 546/82; 514/293; 514/250; 514/214
[58] Field of Search .................. 544/101; 514/230.5, 514/230.2

[56] References Cited

U.S. PATENT DOCUMENTS

| 4,939,138 | 7/1990 | D'Ambra et al. .................. 514/21.8 |
| 5,280,030 | 1/1994 | Jegham et al. .................. 514/322 |

*Primary Examiner*—Matthew V. Grumbling
*Attorney, Agent, or Firm*—Jacobson, Price, Holman & Stern, PLLC

[57] ABSTRACT

A compound of formula (I):

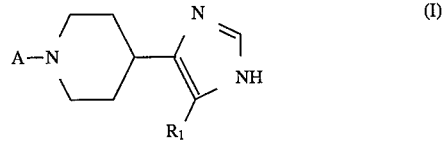

in which

R$_1$ represents a hydrogen atom or a straight or branched (C$_1$–C$_4$)alkyl group; and A represents a 5,6-dihydro-4H-imidazo[4,5,1-ij]quinol-2-yl group, a 4,5-dihydroimidazo[1,5,4-de][1,4]benzoxazin-2-yl group, a 4-methyl-4,5-dihydroimidazo[1,5,4-de][1,4]benzoxazin-2-yl group, a 4-phenyl-4,5-dihydroimidazo[1,5,4-de][1,4]benzoxazin-2-yl group, a 4-phenylmethyl-4,5-dihydroimidazo[1,5,4-de][1,4]benzoxazin-2-yl group, a 5-methyl-4,5-dihydroimidazo[1,5,4-de][1,4]benzoxazin-2-yl group, a 5,6-dihydro-4H-imidazo[1,5,4-de]quinoxalin-2-yl group, a 6-oxo-5,6-dihydro-4H-imidazo[4,5,1-ij]quinol-2-yl group, or a 5-methyl-4,5,6,7-tetrahydroimidazo[4,5,1-jk][1,4]benzodiazepin-2-yl group which may be unsubstituted or substituted in the 6-position by a phenylmethyl group;

or an addition salt thereof with a pharmaceutically acceptable acid.

3 Claims, No Drawings

IMIDAZOL-4-YLPIPERIDINE DERIVATIVES, THEIR PREPARATION AND THEIR APPLICATION IN THERAPEUTICS

The present invention relates to imidazol-4-ylpiperidine derivatives, their preparation and their application in therapeutics.

The present invention provides a compound of formula (I):

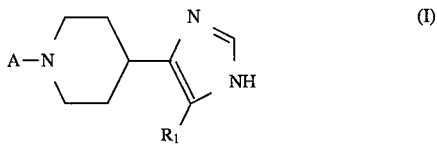

in which

R$_1$ represents a hydrogen atom or a straight or branched (C$_1$–C$_4$)alkyl group; and A represents a 5,6-dihydro-4H-imidazo[4,5,1-ij]quinol-2-yl group, a 4,5-dihydroimidazo[1,5,4-de][1,4]benzoxazin-2-yl group, a 4-methyl-4,5-dihydroimidazo[1,5,4-de][1,4]benzoxazin-2-yl group, a 4-phenyl-4,5-dihydroimidazo[1,5,4-de][1,4]benzoxazin-2-yl group, a 4-phenylmethyl-4,5-dihydroimidazo[1,5,4-de][1,4]benzoxazin-2-yl group, a 5-methyl-4,5-dihydroimidazo[1,5,4-de][1,4]benzoxazin-2-yl group, a 5,6-dihydro-4H-imidazo[1,5,4-de]quinoxalin-2-yl group, a 6-oxo-5,6-dihydro-4H-imidazo[4,5,1-ij]quinol-2-yl group, or a 5-methyl-4,5,6,7-tetrahydroimidazo[4,5,1-jk][1,4]benzodiazepin-2-yl group which may be unsubstituted or substituted in the 6-position by a phenylmethyl group;

or an acid addition salt thereof with a pharmaceutically acceptable acid.

The compounds whose formula is a mesomeric form of the formula (I) form part of the invention. Some compounds of the invention possess an asymmetric carbon and the isomers also form part of the invention.

Compounds of formula (I) in which A represents a benzimidazole group are described in EP-A-0,507,650.

In accordance with the invention, it is possible to prepare the compounds of formula (I) according to the process illustrated in Diagram 1.

A compound of formula (II) in which Z represents a halogen atom, preferably a chlorine atom, and A is as defined above is reacted while hot in a solvent, such as isoamyl alcohol, with a piperidine of formula (III) in which R$_1$ is as defined above.

Diagram 1

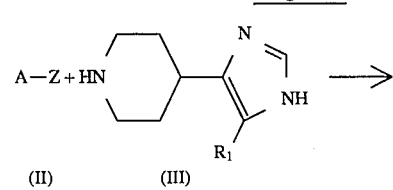

Diagram 1
-continued

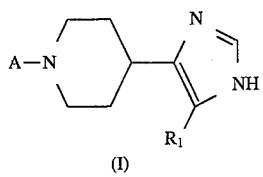

The compound of formula (I) thus obtained is optionally converted into an acid addition salt thereof with a pharmaceutically acceptable acid.

The starting compounds are described in the literature or can be prepared according to methods which are described therein or which are known to those skilled in the art.

Thus, 4-(5-methyl-1H-imidazol-4-yl)piperidine is described in J. Med. Chem., 1986, 29, 2154–63. 4-(1H-Imidazol-4-yl)piperidine is described in Arch. Pharmaz., (Weinheim. Get.) 1973, 306(12), 934–42 and in EP-A-0, 197,840.

1,2,3,4-Tetrahydroquinolin-8-amine is described in Chemical Abstracts, 1939, 33, 610.

5,6-Dihydro-4H-imidazo[4,5,1-ij]quinol-2(1H)-one may be prepared according to a method analogous to that described in J. Org. Chem., 1960, 25, 1138–47 and in Chemical Abstracts, 1965, 63, 13272.

1,1-Dimethylethyl 2-hydroxy-1-methylethylcarbamate may be prepared according to the method described in Tetrahedron Letters, 1991, 47(38), 8177–94.

(S)-9-Nitro-7-chloro-3-methyl-3,4-dihydro-1H-1,4-benzodiazepine-2,5-dione may be prepared according to the method described in J. Med. Chem., 1991, 34(11), 3187–97.

(S)-3-Methyl-2,3,4,5-tetrahydro-1H-1,4-benzodiazepin-9-amine may be prepared according to the method described in J. Med. Chem., 1991, 34(2), 746–51.

(S)-5-Methyl-4,5,6,7-tetrahydroimidazo[4,5,1-jk][1,4]benzodiazepin-2(1H)-one may be prepared according to a method analogous to that described in J. Med. Chem., 1991, 34(2), 747–51 and in J. Med. Chem., 1991, 34(11), 3187–97.

The Examples which follow further illustrate in detail the preparation of compounds according to the invention. The microanalyses and the IR and NMR spectra confirm the structure of the compounds obtained. The numbers of the exemplified compounds refer to those in the table given later which illustrates the structures and the chemical properties of some compounds according to the invention. The ratios in brackets corresponds to the base:salt ratios.

EXAMPLE 1 (Compound No. 1)

2-[4-(1H-Imidazol-4-yl)piperid-1-yl]-5,6-dihydro-4H-imidazo-[4,5,1-ij]quinoline 1.1.
2-Chloro-5,6-dihydro-4H-imidazo[4,5,1-ij]quinoline 1.1.1. 1,2,3,4-Tetrahydroquinolin-8-amine 25 g (0.169 mol) of quinolin-8-amine are dissolved in 600 ml of ethanol. The reaction mixture is heated to 70° C. and 45 g of sodium are added in small pieces. The mixture is brought to the reflux temperature until the sodium has disappeared. The mixture is then evaporated to dryness and the residue is taken up in an ether/hexane (50/50) mixture, filtered and again evaporated to dryness. 35 g of product are obtained in the form of an oil which is used as is in the following stage.

1.1.2. 5,6-Dihydro-4H-imidazo[4,5,1-ij]quinol-2(1H)-one 13 g (0.216 mol) of urea are added to 32 g (0.216 mol) of 1,2,3,4-tetrahydroquinolin-8-amine and the mixture is heated for 3 hours at 180° C. Boiling water is added, the reaction mixture is allowed to cool, ether is added and the mixture is stirred for 2 hours. The reaction mixture is then filtered, the precipitate is sucked dry, washed successively with water and ether and dried under vacuum. There are obtained 19 g of product which is recrystallized from isopropanol. The residue is purified by chromatography on a column of silica gel, the eluent being a dichloromethane/methanol (95/5) mixture. There are obtained 7 g of product which is used as is in the following stage.

Melting point=212° C.

1.1.3. 2-Chloro-5,6-dihydro-4H-imidazo[4,5,1-ij]quinoline 7.6 g (0.0436 mol) of 5,6-dihydro-4H-imidazo[4,5,1-ij]quinol-2(1H)-one are heated in the presence of 70 ml of phosphoryl chloride at the reflux 20 temperature for 3 hours. The solvent is evaporated to dryness and the residue is taken up in ice. The pH of the reaction mixture is adjusted to 8 with a concentrated sodium hydroxide solution and extraction is carried out with dichloromethane. The organic phase is dried over sodium sulphate and the solvent evaporated to dryness. The residue is purified by chromatography on a column of silica gel, the eluent being an ethyl acetate/hexane (30/70) mixture. There are obtained 5.8 g of product which is used as is in the following stage.

Melting point=85°–87° C.

1.2. 2-[4-(1H-Imidazol-4-yl)piperid-1-yl]-5,6-dihydro-4H-imidazo-[4,5,1-ij]quinoline 1 g (0.0052 mol) of 2-chloro-5,6-dihydro-4H-imidazo[4,5,1-ij]quinoline, 1.57 g (0.0104 mol) of 4-(1H-imidazol-4-yl)piperidine and 5 ml of isoamyl alcohol are heated at 120° C. for 1 day. The alcohol is then evaporated to dryness, the residue is taken up in a water/ether (50/50) mixture and the product sucked dry. The product is purified by chromatography on a column of silica gel, the eluent being a dichloromethane/methanol/aqueous ammonia (95/5/0.5) mixture, is then triturated in ether and dried under vacuum at 60° C. 1 g of product is obtained.

Melting point=250°–255° C.

EXAMPLE 2 (Compound No. 8)

4-Methyl-2-[4-(5-methyl-1H-imidazol-4-yl)piperid-1-yl]-4,5-dihydroimidazo[1,5,4-de][1,4]benzoxazine (Z)-but-2-enedioate (1:2)

2.1. 2-Chloro-4-methyl-4,5-dihydroimidazo[1,5,4-de][1,4]benzoxazine

2.1.1. 1,1-Dimethylethyl 2-hydroxy-1-methylethylcarbamate

A suspension of 7.5 g (0.1 mol) of 2-aminopropan-1-ol in 100 ml of a 1N sodium hydroxide solution and 100 ml of dichloromethane is cooled in an ice bath and 22.8 g (0.105 mol) of bis(1,1-dimethylethyl) dicarbonate in solution in 20 ml of dichloromethane are added little by little. The temperature of the reaction mixture is left to return to room temperature and the mixture is stirred for one night. After separation by settling, the organic phase is recovered and washed twice with water. Drying is carried out and the solvent evaporated to dryness. There are obtained 15 g of product which is recrystallized by trituration in hexane.

2.1.2. 1-(2-Chloro-3-nitrophenoxy)propan-2-amine 7.2 g (0.0414 mol) of 1,1-dimethylethyl 2-hydroxy-1-methylethylcarbamate and 10.8 g (0.0414 mol) 15 of triphenylphosphine are placed in a 500 ml, three-necked, round-bottomed flask containing 140 ml of benzene. The mixture is cooled in an ice bath and 6.5 ml (0.0414 mol) of diethyl azodicarboxylate are added dropwise. The mixture is left stirring for 15 minutes, 4.8 g (0.027 mol) of 2-chloro-3-nitrophenol are added, the temperature of the reaction mixture is left to return to room temperature and the reaction mixture is left stirring overnight. The precipitate obtained is then filtered and the filtrate evaporated. The residue is taken up in 100 ml of a 3N hydrochloric acid solution and is then heated at 80° C. in an oil bath for 2 hours. The phases are separated, the aqueous phase is recovered, the pH is adjusted to alkaline with a concentrated sodium hydroxide solution and extraction is carried out three times with ether. Washing is carried out with water and drying is carried out. There are obtained 6 g of product which is used as is in the following stage.

2.1.3 3-Methyl-5-nitro-3,4-dihydro-2H-1,4-benzoxazine 6 g (0.026 mol) of 1-(2-chloro-3-nitrophenoxy)propan-2-amine, 3.6 g (0.026 mol) of potassium carbonate and 20 ml of N,N-dimethylformamide are heated at 110° C. with stirring overnight. The reaction mixture is poured into water and extracted 3 times with ether. The organic phase is recovered, washed with water, dried and the solvent evaporated to dryness. There are obtained 4 g of product in the form of a crystalline residue which is used as is in the following stage.

Melting point=60° C.

2.1.4 3-Methyl-3,4-dihydro-2H-1,4-benzoxazin-5-amine 4 g (0.0205 mol) of 3-methyl-5-nitro-3,4-dihydro-2H-1,4-benzoxazine in solution in 100 ml of ethanol are placed in a Parr apparatus. A catalytic hydrogenation is carried out in the presence of 5% palladium-on-charcoal at room temperature under a pressure of 30 psi. The catalyst is filtered, washed with ethanol, the filtrate recovered and the solvent evaporated to dryness. There are obtained 3.3 g of product which is used as is in the following stage.

2.1.5. 4-Methyl-4,5-dihydroimidazo[1,5,4-de][1,4]benzoxazin-2(1H)-one 3.3 g (0.02 mol) of 3-methyl-3,4-dihydro-1H-1,4-benzoxazin-5-amine are heated at 160°–165° C. in an oil bath for 1.5 hours in the presence of 1.7 g (0.028 mol) of urea. A solid is obtained which is taken up in a water/ether (50/50) mixture. The phases are separated, the organic phase is recovered, is washed, is dried and the solvent evaporated to dryness. The residue obtained is purified by chromatography on a column of silica gel, the eluent being ethyl ether. 2 g of product are obtained.

Melting point=137° C.

2.1.6 2-Chloro-4-methyl-4,5-dihydroimidazo [1,5,4-de][1,4]benzoxazine 1.9 g (0.01 mol) of 4-methyl-4,5-dihydroimidazo[1,5,4-de][1,4]benzoxazin-2(1H)-one in 35 ml of phosphoryl chloride are heated at the reflux temperature for 2 hours. The solvent is evaporated to dryness and the residue taken up successively in ice-cold water and then in a concentrated aqueous ammonia 25 solution. Extraction is then carried out twice with ether, the organic phases are combined, are dried and evaporated to dryness. The residue is purified by chromatography on a column of silica gel, the eluent being an ethyl acetate/hexane (40/60) mixture. There are obtained 1.5 g of product in the form of an oil which is used as is in the following stage.

2.2. 4-Methyl-2-[4-(5-methyl-1H-imidazol-4-yl) piperid-1-yl]-4,5-dihydroimidazo[1,5,4-de] [1,4]benzoxazine (Z)-but-2-enedioate 1.72 g (0.0072 mol) of 4-(5-methyl-1H-imidazol-4-yl)piperidine, 0.75 g (0.0036 mol) of 2-chloro-4-methyl-4,5-dihydroimidazo[1,5,4-de][1,4]benzoxazine and 4 ml of isoamyl alcohol are heated at 120° C. for 24 hours with stirring. The solvent is then evaporated to dryness, the residue taken up in a water/ether (50/50) mixture and then left stirring until the product has crystallized. The crystalline product is sucked dry, is washed successively with water and with ether and is then purified by chromatography on a column of silica gel, the eluent being a dichloromethane/methanol/aqueous ammonia (95/5/0.5) mixture. The product is recrystallized from ether. The dimaleate is prepared by adding maleic acid to the base in an alcohol/ethyl ether mixture.

Melting point=140° C.

EXAMPLE 3 (Compound No. 8a)

(S)-4-Methyl-2-[4-15-methyl-1H-imidazol-4-yl)piperid-1-yl]-4,5-dihydroimidazo[1,5,4-de][1,4]benzoxazine (Z)-but-2-enedioate (1:2)

3.1 (S)-2-Chloro-4-methyl-4,5-dihydroimidazo [1,5,4-de][1,4]benzoxazine

This compound is obtained from (S)-2-aminopropan-1-ol according to the method described in Example 2.1

3.2. (S) -4-Methyl-2-[4-(5-methyl-1H-imidazol-4-yl) piperid-1-yl]-4,5-dihydroimidazo[1,5,4-de] [1,4]benzoxazine (Z)-but-2-enedioate (1:2)

This compound is prepared from (S)-2-chloro-4-methyl-4,5-dihydroimidazo[1,5,4-de][1,4]benzoxazine and 4-(5-methyl-1H-imidazol-4-yl)piperidine according to the method described in Example 2.2. There are obtained 2.1 g of compound in the base form which crystallizes from a dichloromethane/ether mixture.

$[a]_D^{20}$:–20.8° (c=0.01, methanol). The maleate is prepared by adding maleic acid to the base in a methanol/ether mixture and the product is then dried at 100° C.

Melting point=136–140° C.

$[\alpha]_D^{20}$=8.3° (c=0.01, methanol)

EXAMPLE 4 (Compound No. 8b)

(R) -4-Methyl-2-[4-(5-methyl-1H-imidazol-4-yl) piperid-1-yl]-4,5-dihydroimidazo[1,5,4-de] [1,4]benzoxazine (Z)-but-2-enedioate (1:2)

4.1 (R) -2-Chloro-4-methyl-4,5-dihydroimidazo[1,5,4-de] [1,4]benzoxazine

This compound is obtained from (R)-2-aminopropan-1-ol according to the method described in Example 2.1.

4.2. (R)-4-Methyl-2-[4-(5-methyl-1H-imidazol-4-yl) piperid-1-yl]-4,5-dihydroimidazo[1,5,4-de] [1,4]benzoxazine (Z)-but-2-enediote (1:2)

This compound is obtained from (R)-2-chloro-4-methyl-4,5-dihydroimidazo[1,5,4-de][1,4]benzoxazine and 4-(5-methyl-1H-imidazol-4-yl)piperidine according to the method described in Example 2.2. The compound is obtained in the base form which crystallizes from a dichloromethane/ether mixture.

Melting point=143° C.

$[\alpha]_D^{20}$=+22° (c=0.01, methanol)

The maleate is prepared by adding maleic acid to the base in a methanol/ether mixture and the product is then dried at 100° C.

Melting point=136°–140° C.

$[\alpha]_D^{20}$=+8.6° (c=0.01, methanol).

EXAMPLE 5 (Compound No. 7a)

(S) -4-Methyl-2-[4-(1H-imidazol-4-yl)piperid-1-yl)-4,5-dihydroimidazo[1,5,4-de][1,5,4]-benzoxazine (Z)-but-2-enedioate (1:2)

This compound is obtained from (S)-2-chloro-4-methyl-4,5-dihydroimidazo[1,5,4-de][1,4]benzoxazine and 4-(1H-imidazol-4-yl)piperidine according to the method described in Example 2. The compound is obtained in the base form.

Melting point=210°–212° C. ][$\alpha]_D^{20}$=–61.9° (c=0.01, methanol) .

The maleate is prepared according to the method described in Example 2.

Melting point=156° C.

$[\alpha]_D^{20}$=–8.8° (c=0.01, methanol)

EXAMPLE 6 (Compound No. 7b)

(R) -4-Methyl-2-[4-(1H-imidazol-4-yl)piperid-1-yl)-4,5-dihydroimidazo[1,5,4-de][1,5,4]-benzoxazine (Z)-but-2-enedioate (1:2)

This compound is obtained from (R)-2-chloro-4-methyl-4,5-dihydroimidazo [1,5,4-de][1,4]benzoxazine and 4-(1H-imidazol-4-yl)piperidine according to the method described in Example 2. The compound is obtained in the base form.

Melting point=212° C.

[α]$_D^{20}$=+59.9° (c=0.01, methanol).

The maleate is prepared according to the method described in Example 2.

Melting point=156° C.

[α]$_D^{20}$=+9.6° (c=0.01, methanol)

EXAMPLE 7 (Compound No. 11a)

(S) -2-[4-(1H-Imidazol-4-yl)piperid-1-yl]-4-phenyl-4,5-dihydroimidazo[1,5,4-de][1.4]benzoxazine This compound is prepared from 1,1-dimethylethyl (S)-2-hydroxy-1-phenylethylcarbamate and 4-(1H-imidazol-4-yl)piperidine according to the procedure described in Example 2. The product is obtained in the base form.

Melting point=135°–140° C.

[α]$_D^{20}$=+108 2° (c=0.01, methanol)

EXAMPLE 8 (Compound No. 11b)

(R)-2-[4-(1H-Imidazol-4-yl)piperid-1-yl]-4-phenyl-4,5-dihydroimidazo[1,5,4-de][1,4]benzoxazine This compound is prepared from 1,1-dimethylethyl (R)-2-hydroxy-1-phenylethylcarbamate and 4-(1H-imidazol-4-yl)piperidine according to the procedure described in Example 2. The product is obtained in the base form.

Melting point=135°–140° C.

[α]$_D^{20}$=–114° (c=0.01, methanol).

EXAMPLE 9 (Compound No. 12a)

(S)-2-[4-(5-Methyl-1H-imidazol-4-yl)piperid-1-yl]-4-phenyl-4,5-dihydroimidazo[1,5,4-de][1,4]-benzoxazine This compound is obtained from 1,1-dimethylethyl (S)-2-hydroxy-1-phenylethylcarbamate and 4-(5-methyl-1H-imidazol-4-yl)piperidine according to the procedure described in Example 2. The product is obtained in the base form.

Melting point=206° C.

[α]$_D^{20}$=+95.2° (c=0.01, methanol)

EXAMPLE 10 (Compound No. 12b)

(R)-2-[4-(5-Methyl-1H-imidazol-4-yl)piperid-1-yl]-4-phenyl-4,5-dihydroimidazo[1,5,4-de][1,4]-benzoxazine This compound is obtained from 1,1-dimethylethyl (R)-2-hydroxy-1-phenylethylcarbamate and 4-(5-methyl-1H-imidazol-4-yl)piperidine according to the procedure described in Example 2. The product is obtained in the base form.

Melting point=206° C.

[α]$_D^{20}$=–98.1° (c=0.01, methanol)

EXAMPLE 11 (Compound No. 14)

2-[4-(1H-Imidazol-4-yl)piperid-1-yl]-5,6-dihydro-4H-imidazo[1,5,4-de]quinoxaline ethanedioate (1:1.5)

11.1. 2-Chloro-5,6-dihydro-4H-imidazo[1,5,4-de]quinoxaline 11.1.1. 2-[(2,6-Dinitrophenyl)amino]ethanol 25 g (0.123 mol) of 1-chloro-2,6-dinitrobenzene are placed in a three-necked, round-bottomed flask containing 180 ml of ethanol. The reaction mixture is heated to 70° C., 22.3 g (0.365 mol) of ethanolamine are added dropwise over 15 minutes and the mixture is left stirring at this temperature for 30 minutes. The temperature of the reaction mixture is left to return to room temperature and 1 liter of water is then added. The product crystallizes, is sucked dry, is washed with water and is dried. There are obtained 25 g of product which is used as is in the following stage.

Melting point=77° C.

11.1.2. 2-[(2,6-Diaminophenyl)amino]ethanol dihydrochloride 18.3 g (0.0805 mol) of 2-[(2,6-dinitrophenyl)amino]ethanol in a solution containing 144 g of stannous chloride dihydrate in 146 ml of a concentrated hydrochloric acid solution are heated at 80° C. in an oil bath for 15 minutes. The reaction mixture is cooled in an ice bath, 460 ml of a concentrated sodium hydroxide solution are slowly added and then extraction is carried out three times with dichloromethane. The organic phases are combined, are dried and evaporated to dryness.

The product is obtained in the base form.

The hydrochloride is prepared from an alcohol/ethereal hydrochloric acid mixture.

The hydrochloride is obtained which is used as is in the following stage.

Melting point=195°–200° C.

11.1.3. 1,2,3,4-Tetrahydroquinoxalin-5-amine 25 g (0.104 mol) of 2-[(2,6-diaminophenyl)amino]ethanol dihydrochloride are heated at 160° C. for 3 hours in 300 ml of a 62% hydrobromic acid solution. The reaction mixture is cooled to –20° C. until crystallization takes place and the precipitate obtained is dried, under nitrogen, with a mixture of methanol and ether. It is taken up in water, the pH is adjusted to alkaline with a concentrated sodium hydroxide solution and extraction is carried out with a dichloromethane/ether (50/50) mixture. Drying and evaporation are carried out.

There are obtained 11.5 g of product which is used as is in the following stage.

11.1.4 5,6.-Dihydro-4H-imidazo[1,5,4-de]quinoxalin-2(1H)-one 11.5 g (0.078 mol) of 1,2,3,4-tetrahydro-quinoxalin-5-amine are heated at 160°–165° C. in an oil bath for 2 hours in the presence of 6.7 g (0.028 mol) of urea. A solid is obtained which is taken up in 20 ml of water. The mixture is cooled in an ice bath and the precipitate obtained is sucked dry, washed with water and dried. The residue is purified by chromatography on a column of silica gel, the eluent being a dichloromethane/methanol/aqueous ammonia (95/5/0.5)

mixture. There are obtained 5.5 g of product which crystallizes from ethanol.

Melting point=206° C.

11.1.5.
2-Chloro-5,6-dihydro-4H-imidazo[1,5,4-de]quinoxaline 3 g (0.0155 mol) of 5,6-dihydro-4H-imidazo[1,5,4-de]quinoxalin-2(1H)-one in 60 ml of phosphoryl chloride are heated at the reflux temperature for 3 hours. The solvent is evaporated to dryness and the residue taken up successively in ice-cold water and in a concentrated aqueous ammonia solution. Extraction is then carried out twice with ether and the organic phases are combined, dried and evaporated to dryness. The residue is purified by chromatography on a column of silica gel, the eluent being ether. There are obtained 1.8 g of product in the oil form which is used as is in the following stage.

11.2.
2-[4-(1H-Imidazol-4-yl)piperid-1-yl]5,6-dihydro-4H-imidazo[1,5,4-de]quinoxaline ethanedioate (1:1.5)

The reaction is carried out from 2-chloro-5,6-dihydro-4H-imidazo[1,5,4-de]quinoxaline and 4-(1H-imidazol-4-yl)piperidine according to the method described in Example 1.2. There is obtained 0.95 g of product in the base form. It is recrystallized from an alcohol/ether mixture, is dissolved in methanol and the oxalate is prepared.

Melting point=212° C.

EXAMPLE 12 (Compound No. 19)

(S)-5-Methyl-2-[4-(5-methyl-1H-imidazol-4-yl)piperid-1-yl]-4,5,6,7-tetrahydroimidazo[4,5,1-jk][1,4]benzodiazepine (E)-but-2-enedioate (1:2)

12.1.
(S)-2-Chloro-5-methyl-4,5,6,7-tetrahydroimidazo[4,5,1-jk][1,4]benzodiazepine

12.1.1. (S)-9-Amino-3-methyl-3,4-dihydro-1H-1,4-benzodiazepine-2,5-dione 6 g (0.022 mol) of (S)-7-chloro-3-methyl-9-nitro-3,4-dihydro-1H-1,4-benzodiazepine-2,5-dione, 200 ml of water, 200 ml of acetic acid and 0.5 g of 5% palladium-on-charcoal are placed in a Parr bottle. The catalytic hydrogenation is carried out under 40 psi at 50° C. The catalyst is filtered, is washed with an acetic acid/water (50/50) mixture and the filtrate is concentrated to dryness. It is taken up in water and the pH adjusted to alkaline with a sodium carbonate solution. The mixture is left stirring for 15 minutes, filtration is carried out, drying is carried out and the solvent evaporated to dryness. 4 g of product are obtained.

Melting point=320° C.

12.1.2. (S)-3-Methyl-2,3,4,5-tetrahydro-1H-1,4-benzodiazepin-9-amine 14.8 g (0.072 mol) of (S)-9-amino-3-methyl-3,4-dihydro-1H-1,4-benzodiazepine-2,5-dione in 455 ml of dioxane are heated at the reflux temperature with stirring for 48 hours in the presence of 17 g of lithium aluminium hydride. The reaction mixture is cooled in an ice bath and then, slowly and successively, 17 ml of water, 17 ml of a 5N sodium hydroxide solution and 45 ml of water are added. The mixture is left stirring for 2 hours at room temperature, filtration is carried out and washing is carried out with hot tetrahydrofuran and with dichloromethane. The organic phase is recovered and is concentrated. There are obtained 12.7 g of product which is used as is in the following stage.

12.1.3. (S)-5-Methyl-4,5,6,7-tetrahydroimidazo[4,5,1-jk][1,4]benzodiazepin-2(1H)-one 300 ml of dichloromethane and 22.8 ml of 4-methylmorpholine are added to 12.7 g (0.072 mol) of (S)-3-methyl-2,3,4,5-tetrahydro-(1H)-1,4-benzodiazepin-9-amine. The mixture is then poured into a solution of 9.1 ml (0.0072 mol) of trichloromethyl chloroformate in 340 ml of dichloromethane cooled beforehand with an ice bath. The mixture is left stirring for 10 minutes at 0° C. and then for 20 minutes at room temperature. The solvent is evaporated under vacuum and the residue taken up in 200 ml of water and 34 ml of dioxane. The mixture is heated in a water bath for 45 minutes and then a concentrated aqueous ammonia solution is added. The mixture is left to cool, is sucked dry, is washed with water and is dried under vacuum. There are obtained 11.5 g of product which is recrystallized from boiling water. There are obtained 7.6 g of product which is used as is in the following stage.

Melting point=198°–203° C.

12.1.4. (S)-2-Chloro-5-methyl-4,5,6,7-tetrahydro-imidazo[4,5,1-jk][1,4]benzodiazepine 4.55 g (0.022 mol) of (S)-5-methyl-4,5,6,7-tetrahydroimidazo[4,5,1-jk][1,4]benzodiazepin-2(1H)-one in 90 ml of phosphoryl chloride are heated at 130° C. in an oil bath for 4 hours. The solvent is evaporated under vacuum and the oily residue taken up while hot in water. The mixture is left stirring for 15 minutes, is cooled and a concentrated aqueous ammonia solution is added. Extraction is carried out with dichloromethane, washing is carried out with water, drying is carried out over sodium sulphate and the solvent is evaporated to dryness. There are obtained 4.3 g of product in the form of an oil which is used as is in the following stage.

12.2. (S)-5-Methyl-2-[4-(5-methyl-1H-imidazol-4-yl)piperid-1-yl]-4,5,6,7-tetrahydroimidazo[4,5,1-jk][1,4]benzodiazepine (E)-but-2-enedioate (1:2)

2.36 g (0.0072 mol) of 4-(5-methyl-1H-imidazol-4-yl)piperidine and 1.5 g (0.0071 mol) of (S)-2-chloro-5-methyl-4,5,6,7-tetrahydroimidazo[4,5,1-jk][1,4]benzodiazepine in 8 ml of isoamyl alcohol are heated at 120° C. in an oil bath for 15 hours. The solvent is then evaporated and the residue purified by chromatography on a column of silica gel, the eluent being a dichloromethane/methanol/aqueous ammonia (95/5/0.5) mixture. The pure fractions are collected, are concentrated under vacuum and the product is crystallized from acetone. There is obtained 0.4 g of product in the base form. The difumarate is prepared by adding fumaric acid to the base in ethanol. It is recrystallized from methanol. There is obtained 0.4 g of product in the difumarate form.

Melting point=196°–198° C.

$[\alpha]_D^{20}=+1°$ (c=0.01, methanol)

EXAMPLE 13 (Compound No.

(S) -2-[4-(1H-Imidazol-4-yl) piperid-1-yl-5-methyl-4,5,6,7-tetrahydroimidazo [4,5,1-jk][1,4]benzodiazepine (Z) -but-2-enedioate (1:3)

4.9 g (0.0324 mol) of 4-(1H-imidazol-4-yl)piperidine and 4.3 g (0.0193 mol) of (S)-2-chloro-5-methyl-4,5,6,7-tetrahydroimidazo [4,5,1-jk][1,4]benzodiazepine in 15 ml of isoamyl alcohol are heated at 120° C. in an oil bath for 12 hours. The solvent is then evaporated and the residue is purified by chromatography on a column of silica gel, the eluent being a dichloromethane/methanol/aqueous ammonia (93/7/0.7) mixture. The pure fractions are collected, are concentrated under vacuum and the product is crystallized from 15 ml of boiling acetone. It is sucked dry, it is washed with acetone and is dried. There are obtained 2.8 g of product in the base form. The maleate is prepared by adding maleic acid to the base in an alcohol/ether mixture. The product is recrystallized in the salt form from a methanol/ether mixture.

Melting point=132°–134° C.
$[\alpha]_D^{20}=+2°$ (0.005, methanol)

EXAMPLE 14 (Compound No. 20)

(S) -2-[4-(1H-Imidazol-4-yl)piperid-1-yl]-5-methyl-6-phenylmethyl-4,5,6,7-tetrahydroimidazo [4,5,1-jk][1,4]benzodiazepine (Z)-but-2-enedioate (1:2)

0.16 g (0.00134 mol) of (bromomethyl)benzene is added to a suspension of 0.45 g (0.0013 mol) of (S)-2-[4-(1H-imidazol-4-yl)piperid-1-yl]-5-methyl-4,5,6,7-tetrahydroimidazo[4,5,1-jk][1,4]benzodiazepine in 4.5 ml of ethanol containing 0.035 g (0.00253 mol) of potassium carbonate. The mixture is heated at 60° C. in an oil bath for 2 hours and the solvent is then evaporated to dryness. The residue is purified by chromatography on a column of silica gel, the eluent being a dichloromethane/methanol/aqueous ammonia (95/5/0.5) mixture. There is recovered 0.3 g of product in the base form. The dimaleate is prepared by adding maleic acid to the base in acetone. It is sucked dry, it is washed with acetone and is dried.

Melting point=160°–162° C.
$[\alpha]_D^{20}=+1.1°$ (c=0.01, methanol)

TABLE

| No. | A | $R_1$ | M.p. (°C.) | Salt | $[\alpha]_D^{20}$ (*) |
|---|---|---|---|---|---|
| 1 | (tetrahydroquinoline-imidazole) | –H | 250–255 | — | — |
| 2 | (tetrahydroquinoline-imidazole) | –CH$_3$ | 231–233 | — | — |
| 3 | (tetrahydroquinoline-imidazole) | –CH$_2$CH$_3$ | 219–221 | — | — |
| 4 | (tetrahydroquinoline-imidazole) | –CH(CH$_3$)$_2$ | 175–177 | — | — |

TABLE-continued (I)

| No. | A | $R_1$ | M.p. (°C.) | Salt | $[\alpha]_D^{20}$ (*) |
|---|---|---|---|---|---|
| 5 | (benzoxazine with -OCH2CH2-N) | —H | 172 | mal. (1:2) | — |
| 6 | (benzoxazine with -OCH2CH2-N) | —CH₃ | 150 | mal. (1:2) | — |
| 7 | (benzoxazine with -OCH2CH(CH3)-N) | —H | 148 | mal. (1:2) | — |
| 7a | (benzoxazine with -OCH2CH(CH3)-N) | —H | 156 | mal. (1:2) | −8.8 |
| 7b | (benzoxazine with -OCH2CH(CH3)-N, other enantiomer) | —H | 156 | mal. (1:2) | +9.6 |
| 8 | (benzoxazine with -OCH2CH(CH3)-N) | —CH₃ | 140 | mal. (1:2) | — |
| 8a | (benzoxazine with -OCH2CH(CH3)-N) | —CH₃ | 136–140 | mal. (1:2) | −8.3 |
| 8b | (benzoxazine with -OCH2CH(CH3)-N, other enantiomer) | —CH₃ | 136–140 | mal. (1:2) | +8.6 |

TABLE-continued $$\text{(I)}\quad A-N\underset{R_1}{\overset{}{\bigcirc}}\!\!\!-\!\!\!\overset{N}{\underset{NH}{\diagdown\!\!\!\diagup}}$$

| No. | A | $R_1$ | M.p. (°C.) | Salt | $[\alpha]_D^{20}$ (*) |
|---|---|---|---|---|---|
| 9 | benzimidazole-N-CH₂-CH(CH₃)-O- (linked to benzo ring) | —H | 184–185 | mal. (1:2) | — |
| 10 | benzimidazole-N-CH₂-CH(CH₃)-O- (linked to benzo ring) | —CH₃ | 239–241 | ox. (1:2) | — |
| 11a | benzimidazole-N-CH(Ph)-CH₂-O- (R) | —H | 135–140 | — | +108.2 |
| 11b | benzimidazole-N-CH(Ph)-CH₂-O- (S) | —H | 135–140 | — | −114 |
| 12a | benzimidazole-N-CH(Ph)-CH₂-O- (R) | —CH₃ | 206 | — | +95.2 |
| 12b | benzimidazole-N-CH(Ph)-CH₂-O- (S) | —CH₃ | 207 | — | −98.1 |

TABLE-continued (I) structure: A—N(piperidine)—[imidazole with R₁]

| No. | A | R₁ | M.p. (°C.) | Salt | $[\alpha]_D^{20}$ (*) |
|---|---|---|---|---|---|
| 13 | (2-methylbenzimidazole with N-CH(CH₂Ph)CH₂O- fused) | —CH₃ | 210–212 | fum. (1:1) | −59.9 |
| 14 | (2-methyl-benzimidazole with NH-CH₂CH₂- fused) | —H | 212 | ox. (1:1:5) | — |
| 15 | (2-methyl-benzimidazole with NH-CH₂CH₂- fused) | —CH₃ | 212 | ox. (1:1) | — |
| 16 | (benzimidazole with O=C-CH₂CH₂- fused) | —H | 200 | — | — |
| 17 | (benzimidazole with O=C-CH₂CH₂- fused) | —CH₃ | 130 | — | — |
| 18 | (benzimidazole with HN-CH(CH₃)-CH₂- fused) | —H | 132–134 | mal. (1:3) | +2 |
| 19 | (benzimidazole with HN-CH(CH₃)-CH₂- fused) | —CH₃ | 196–198 | fum. (1:2) | +1 |

TABLE-continued (I)

| No. | A | $R_1$ | M.p. (°C.) | Salt | $[\alpha]_D^{20}$ (*) |
|---|---|---|---|---|---|
| 20 | (structure with benzyl-N, CH₃, H stereochemistry) | —H | 160–162 | mal. (1:2) | +1.1 |

Key to the table:
in the "Salt" column of the table
(x:y) means x mol of base per y mol of acid, the absence of any mention means that the compound is in the base form,
mal. represents the maleate,
fum. represents the fumarate,
ox. represents the oxalate
in the "$[\alpha]_D^{20}$" column of the table
c = 0.01, methanol except for Compound No. 18 where c = 0.005,
the absence of any mention means that the compound is a racemate.

The compounds of the invention were subjected to pharmacological tests which showed their value as active substances in therapy.

Thus, they were tested for their inhibitory effects on the binding of [$^3$H]quipazine to the type 5-HT$_3$ serotoninergic receptors present in the rat cerebral cortex, according to a variant of the method described by Milburn and Peroutka (J. Neurochem., 52, 1787–1792, 1989).

Male Sprague-Dawley rats weighing 150 to 200 g are used in all the tests. Their cerebral cortex is removed and homogenized in 20 volumes (weight/volume) of 25 mM Hepes buffer or of 25 mM Hepes buffer containing sodium chloride (180 mM), calcium chloride (2.5 mM), potassium chloride (5 mM) and magnesium chloride (1.2 mM) (pH 7.4) using a Polytron™ mill. After centrifugation of the suspension for 10 minutes at 45,000×g, the pellet is resuspended in the initial volume of buffer, where appropriate containing 0.05% of Triton X-100™, and a first incubation is performed for 30 minutes at 37° C. Two further centrifugations are then performed as described above, and the final pellet is taken up in 11.7 volumes of 25 mM Hepes buffer, pH 7.4.

The binding of [$^3$H]quipazine (51.6–69.S Ci/mmol, New England Nuclear, Boston, Mass., USA) is determined by incubating 150 μl of the membrane suspension with the radioligand (0.8 nM) in a final volume of 1 ml for 30 min at 25° C., in the absence or presence of the compound under study. Incubation takes place in the presence of 0.1 μM paroxetine and 1 μM ketanserin. Non-specific binding is determined in the presence of 1 μm ondansetron. After incubation, the test mixture is diluted with 5 ml of ice-cold 50 mM Tris-HCl buffer (pH 7.4 at 0° C.). The membranes are collected by filtration on Whatman GF/B™ filters pretreated with 0.05% of polyethyleneimine, and washed with three volumes of 5 ml of ice-cold 50 mM (Tris-HCl buffer.

The radioactivity retained on the filters is measured by liquid scintillation spectrometry at an efficiency of 50 to 60%.

The results are expressed as the concentration (IC$_{50}$) of the compound under study which inhibits 50% of the binding of [$^3$H]quipazine, determined by a graphic or mathematical method. The compounds of the invention which are most active in this test are characterized by IC$_{50}$ values of between 0.01 nM and 10 nM.

The compounds of the invention were also tested for their effect on the Bezold-Jarisch reflex, that is to say an intense bradycardia, caused by intravenous injection of serotonin. This reflex involves the stimulation of the 5-HT$_3$ specific receptors of the vagus nerve, which causes a depolarization and thus a secretion of acetylcholine which is the natural vagal neurotransmitter. Male Sprague-Dawley rats are anaesthetized with urethane (1 to 25 g/kg intraperitoneally), the blood pressure is measured by virtue of a catheter placed in the carotid artery and pressure pulses are used to activate a cardiotachometer. Cannulae are placed in the two femoral veins in order to facilitate intravenous administration of the products.

Traces are recorded of the dose/response curves of the bradycardia caused by injection of doses of 30 μg/kg of serotonin, before and after injection of the compounds under study.

The compounds of the invention inhibit the bradycardia caused by serotonin by 75% at the dose of 1 μg/kg administered intravenously.

The compounds of the invention were also studied for their affinity with respect to 5-HT$_4$ receptors in the striatum of guinea pigs according to the method described by Grossman et al., Br. J. Pharmacol., (1993), 109, 618–624.

Guinea pigs (Harticy, Charles River) weighing 300 to 400 g are humanely killed and the brain is removed. The striata are excised and are frozen at −80° C. On the day of the experiment, the tissue is defrosted to +4° C. in 3 volumes of 50 mM Hepes-NaOH buffer (pH 7.4 at 20° C.) and is homogenized using a Polytron® mill. The homogenate is centrifuged for 10 minutes at 48,000 g, the pellet is recovered, is resuspended and is recentrifuged under the same conditions. The final pellet is suspended in Hepes-NaOH buffer (30 mg of fresh tissue/ml). This membrane suspension is used as is. 100 μl of the membrane suspension are incubated at 0° C. for 120 minutes, in the presence of 0.1 nM of [$^3$H]GR118808 (specific activity 80–85 Ci/mmol), in a final volume of 1 ml of Hepes-NaOH buffer (50 mM, pH 7.4), in the presence or in the absence of compounds under test. Incubation is halted by filtration through a Whatman GF/B filter pretreated with 0.1% polyethyleneimine, each tube is rinsed with 4 ml of buffer at 0° C. and filtered again. The radioactivity retained on the filters is measured by liquid scintigraphy.

The non-specific binding is determined in the presence of 30 μM serotonin. The specific binding represents 90% of the total radioactivity recovered on the filter. For each concentration of study compound, the percentage of inhibition of the specific binding of [$^3$H]GR118808 and then the concentration of the tested compound which inhibits 50% of the specific binding ($IC_{50}$) are determined. The $IC_{50}$ values of the compounds according to the invention lie between 0.02 and 2 μM.

The results of the biological tests show that the compounds of the invention are ligands for types 5-HT$_3$ and 5-HT$_4$ serotoninergic receptors.

They may hence be used for the treatment and prevention of disorders in which 5-HT$_3$ and 5-HT4 receptors are involved, such as nausea and vomiting, for example following antitumour treatment or the administration of an anaesthetic; disorders of the central nervous system such as schizophrenia, mania, anxiety and depression; disorders of cognition such as senile dementia or Alzheimer's presenile dementia; dyskinesia, pain, migraine and headache; disorders associated with alcohol or drug dependence or withdrawal; disorders of gastrointestinal function such as dyspepsia, peptic ulcer, heartburn, flatulence; disorders of the cardiovascular system and respiratory disorders.

They may also be used for the treatment and prevention of disorders such as diarrhoea, irritable colon, oesophageal reflux, intestinal motor disorders, disorders of intestinal secretion, cystic fibrosis of the pancreas, carcinoid syndrome and incontinence.

Thus the present invention also provides a compound of formula (I) or a pharmaceutically acceptable acid addition salt thereof for use in a method of treatment of the human or animal body by therapy, particularly for use in the prevention or treatment of any one of the above disorders.

The present invention also provides the use of a compound of formula (I) or a pharmaceutically acceptable addition salt thereof in the manufacture of a medicament for the prevention or treatment of any one of the above disorders.

For this purpose, they may be presented in all forms suitable for oral or parenteral administration, such as tablets, dragées, capsules including hard gelatin capsules, suspensions or solutions to be swallowed or injected, in combination with pharmaceutically acceptable excipients. The compounds of the present invention may, for example, be administered in doses that enable 0.005 to 5 mg/kg to be administered 1 to 4 times a day.

The embodiments of the invention, in which an exclusive privilege or property is claimed, are defined as follows:

1. A compound of formula (I):

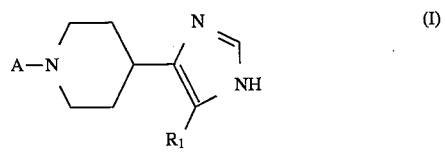

in which

R$_1$ represents a hydrogen atom or a straight or branched (C$_1$–C$_4$)alkyl group; and A represents a 4,5-dihydroimidazo[1,5,4-de][1,4]benzoxazin-2-yl group, a 4-methyl-4,5-dihydroimidazo[1,5,4-de][1,4]benzoxazin-2-yl group, a 4-phenyl-4,5-dihydroimidazo [1,5,4-de][1,4]benzoxazin-2-yl group, a 4-phenylmethyl-4,5-dihydroimidazo[1,5,4-de][1,4]benzoxazin-2-yl group, or a 5-methyl-4,5-dihydroimidazo[1,5,4-de][1,4]benzoxazin-2-yl group, which may be unsubstituted or substituted in the 6-position by a phenylmethyl group;

or an addition salt thereof with a pharmaceutically acceptable acid.

2. A pharmaceutical composition, which comprises a compound according to claim 1 or a pharmaceutically acceptable acid addition salt thereof and a pharmaceutically acceptable excipient.

3. A method of treating or preventing nausea, vomiting, a gastrointestinal disorder selecting from the group consisting of diarrhea, irritable colon, oesophageal reflux, intestinal motor disorder, and a disorder of intestinal secretion, cystic fibrosis of the pancreas, or urinary incontinence, comprising administering to a patient in need thereof an effective amount of the compound of claim 1 or a pharmaceutically acceptable acid addition salt thereof.

* * * * *